United States Patent [19]
Dam

[11] Patent Number: 4,651,555
[45] Date of Patent: Mar. 24, 1987

[54] APPARATUS FOR DETECTING DISCONTINUITIES IN A FLUID STREAM

[75] Inventor: Naim Dam, Oakland Gardens, N.Y.

[73] Assignee: Introtek Corporation, Deer Park, N.Y.

[21] Appl. No.: 649,546

[22] Filed: Sep. 11, 1984

[51] Int. Cl.⁴ .......................................... G01N 29/02
[52] U.S. Cl. .......................................................... 73/19
[58] Field of Search ................................ 73/19, 61 R

[56] References Cited

U.S. PATENT DOCUMENTS

| | | | |
|---|---|---|---|
| 3,921,622 | 11/1975 | Cole | 73/61 R |
| 3,974,681 | 8/1976 | Namery | 73/19 |
| 4,015,464 | 4/1977 | Miller et al. | 73/61 R |
| 4,068,521 | 1/1978 | Cosentino et al. | 73/19 |
| 4,122,713 | 10/1978 | Stasz et al. | 73/19 |
| 4,138,879 | 2/1979 | Liebermann | 73/61 R |
| 4,237,720 | 12/1980 | Abts | 73/19 |
| 4,341,116 | 7/1982 | Bilstad et al. | 73/19 |
| 4,392,374 | 7/1983 | Liebermann | 73/19 |

Primary Examiner—Stephen A. Kreitman
Attorney, Agent, or Firm—Darby & Darby

[57] ABSTRACT

Apparatus for detecting discontinuities, such as bubbles, in a fluid stream in a tube in which successive bursts of ultrasonic energy are transmitted through the tube and received. Discontinuities are detected by comparing each received signal against a reference level which is set over a longer term by the received signals, the presence of a discontinuity is detected by a reduced amplitude signal which causes an indication to be produced.

16 Claims, 3 Drawing Figures

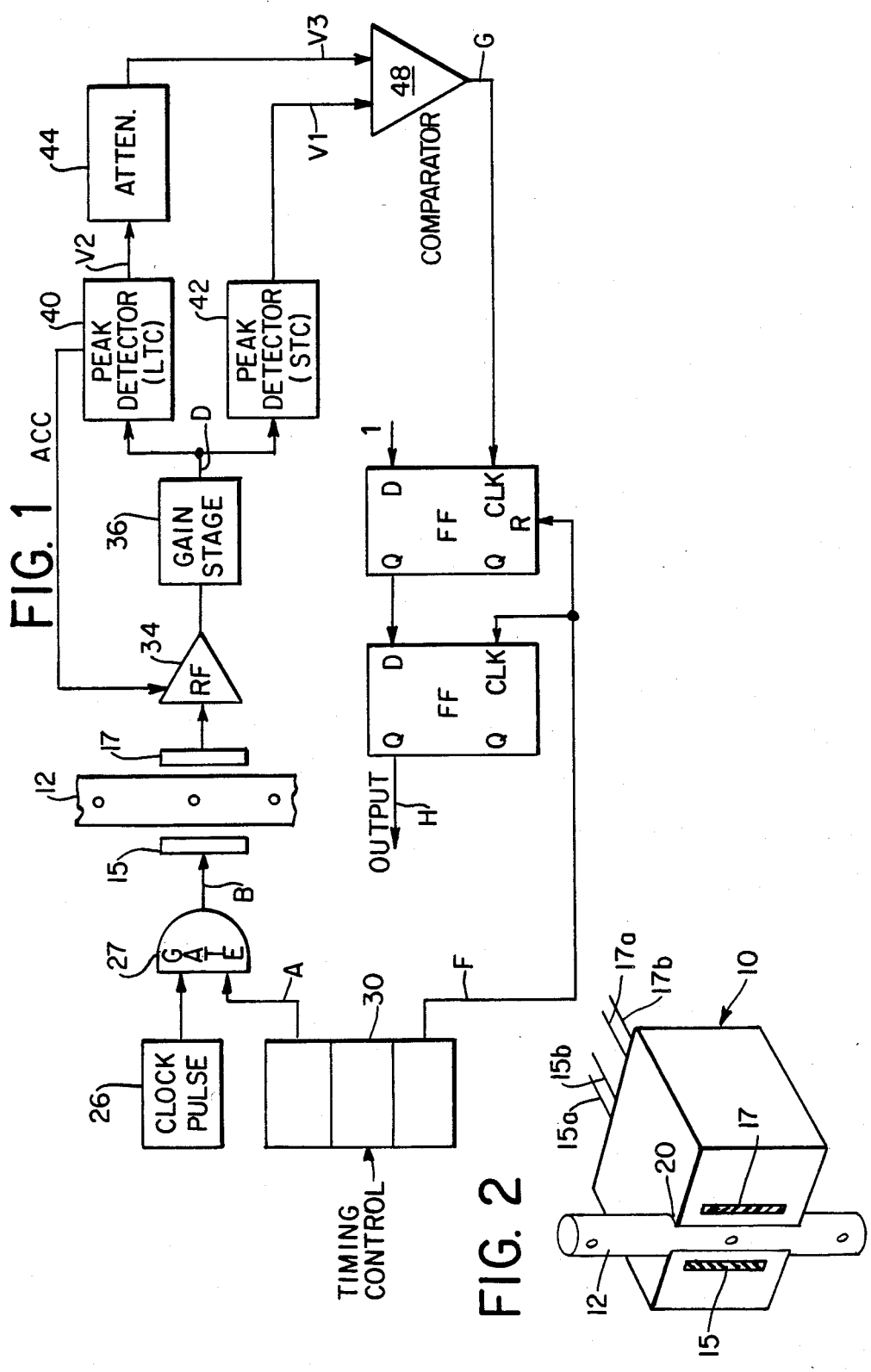

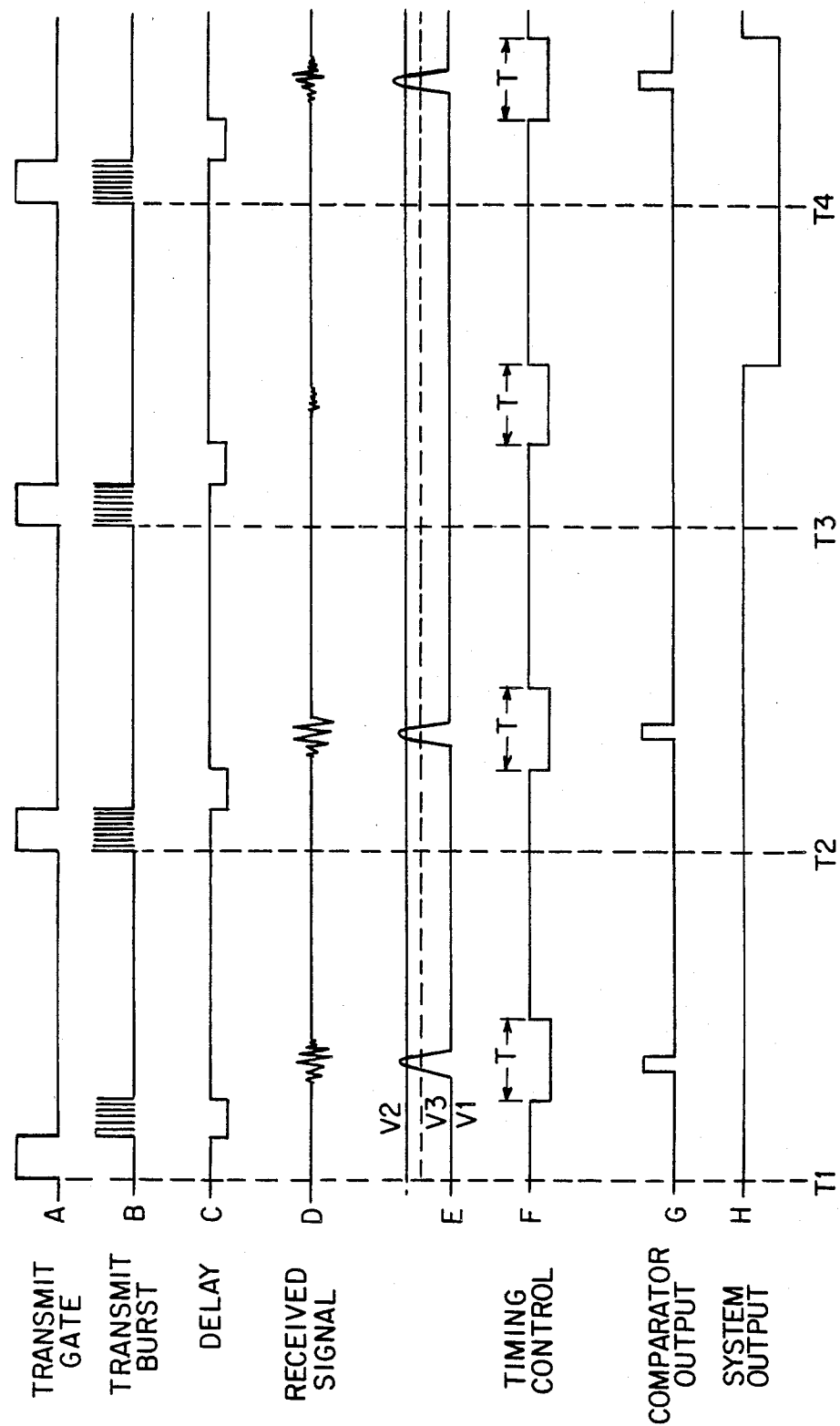

APPARATUS FOR DETECTING DISCONTINUITIES IN A FLUID STREAM

BACKGROUND OF THE INVENTION

This invention relates to apparatus for detecting discontinuities, such as air bubbles, in a fluid flow utilizing ultrasonic energy.

Various arrangements have been proposed for detecting bubbles, discontinuities, such as air particles, solids in a flow of liquid, particularly where the liquid is in a tubing which is either rigid or compressible. Some of the uses for such a discontinuity detector would be, for example, in detecting air bubbles in body fluids, such as blood, which are being transmitted from one place to another either with the patient in the transmittal loop or from one type of a machine, such as blood processing machine, to another such machine.

Various arrangements previously have been provided for such detection. Included among these are, for example, U.S. Pat. No. 3,921,622 to Cole in which bubble detection is accomplished by detecting a change in amplitude of a received ultrasonic pulse versus the amplitude of a pulse which passes through air. Another patent is U.S. Pat. No. 3,974,681 to Namery which uses an amplitude measuring technique, with the components being optimized at particular resonant frequencies of the system.

In the system disclosed in U.S. Pat. No. 4,122,713, to Stasz, a doppler and backscatter technique is used. In Liebermann U.S. Pat. No. 4,138,879, bubbles are detected by transmitting ultrasonic signals through a tube from one transducer to another with an amplifier being maintained in a marginally oscillatory condition. The detection of the bubbles changes the operating state of the system, and the change of state is detected.

In Bilstad U.S. Pat. No. 4,341,116 an arrangement is used in which amplitude levels are detected by a comparator. Liebermann U.S. Pat. No. 4,392,374 uses an adjustable bandpass technique while Abts U.S. Pat. No. 4,237,720 utilizes an ultrasonic transducer as a focusing lens. Another patent of interest is U.S. Pat. No. 4,068,521 to Cosentino et al, in which both continuous wave and pulses of ultrasonic energy can be used. The reception or non-reception of the energy is determined on an amplitude basis.

Some of the aforementioned bubble detectors, particularly those detecting on the basis of amplitude of received signal, have a problem in detecting the bubbles due to the size of the tube in which the fluid flows, the aging of the tube, which reduces its wall thickness and its flexibility, tube wall thickness and also with respect to bubble size. All of these problems give rise to variations in amplitude of the detected received signal. For a constant gain and constant threshold circuit, reliable detection of an air bubble becomes a difficult problem.

BRIEF SUMMARY OF THE INVENTION

In accordance with the invention, a system is provided for detecting discontinuities such as bubbles or particles, in a fluid, e.g. liquid stream. The system includes a circuit for transmitting successive bursts of sonic energy through the tube and a circuit for receiving the successive bursts of sonic signals and processing the into electrical signals. An adaptive signal reference level setting and comparing circuit is provided in which a first portion of the circuit establishes a reference level corresponding to the long term average amplitude of the bursts of sonic energy transmitted through the tube and the liquid. The electrical signal corresponding to each burst is compared against the reference level by a comparator circuit. A signal corresponding to a burst which is transmitted through an air bubble or particle will be of reduced amplitude and this is detected by the comparator circuit which produces an output signal corresponding to either the presence of liquid or a discontinuity in the stream. This output signal is applied to a logic circuit which is configured to produce an indication corresponding to the status of the liquid in the tube.

OBJECTS OF THE INVENTION

Accordingly, it is an object of the present invention to provide an apparatus for detecting discontinuities in a fluid stream.

Another object is to provide apparatus for detecting discontinuities is a fluid stream flowing in a tube in which the amplitude of each of successive bursts of some energy transmitted through the tube is compared against a reference level signal established by the bursts themselves.

Other objects and advantages of the present invention will become more apparent upon reference in the following specification and annexed drawings in which:

BRIEF DESCRIPTION OF THE DRAWINGS

FIG. 1 is a schematic block diagram of the discontinuity detecting system;

FIG. 2 is a perspective view of the sensor head shown partially broken away; and FIG. 3 is a combined timing and signal diagram of various points of the circuit of FIG. 1.

DETAILED DESCRIPTION OF THE INVENTION

Referring to FIG. 1, the overall system includes a sensor head 10 (FIG. 2) into which a tube 12, usually of flexible material, such as plastic, rubber, etc. is to be inserted. The details of the sensor head are shown in FIG. 2 and it includes a sonic energy (ultrasonic) transmit crystal 15 and a receive crystal 17, both of which are of piezoelectric material as is conventional in the art. These crystals 15,17 are fixed in a block of material, such as epoxy resin, on opposite sides of and adjacent to a gap 20 in which the tube 12 is placed. The gap 20 is of a size slightly smaller than the diameter of the tube 12 so that a slight amount of pressure can be applied thereto and the wall of the tube flattened slightly when placed in the sensing gap 20. This provides good contact between the tube and the walls of the sensor head on each side of the gap 20 so that ultrasonic energy from the transmit and receive crystals can be transmitted through the tube without the use of coupling compound. The tube is placed in the gap 20 by pressing it in and removed by pulling it out. Generally, no clamps are needed. The remainder of the sensor head is of epoxy or some other similar material. It should be understood that the sensor head also can be made to accommodate rigid tubing, e.g. glass. In this case, a clamping arrangement could be used.

The height of the head is made somewhat higher than the height of the crystals so that the tube 12 can be held in the sensor head. A respective signal lead is connected to an electrode (not shown) plated on the front and back of each of the crystals. This is also conventional and the electrodes are not shown. The signal lead pairs are designated 15a, 15b and 17a, 17b for the respective crystals. The leads are not shown in the schematic diagram of FIG. 1.

Referring to FIG. 3, the transmit crystal 15 is supplied with bursts of energy from a suitable source which can be, for example, a clock pulse generator 26 which is gated on for a predetermined time or which, as shown, has its output applied to one input of a gate circuit 27 to which a gating pulse is applied for a predetermined time. The frequency of the clock pulses is dependent upon the wall thickness and diameter of the tube 12 and the characteristics of the liquid, e.g. its viscosity, which flows in the tube. In general, clock pulses in the range of 3-5 Mhz have been found suitable but other frequencies can be used.

The gating pulses for gate 27 are supplied from a timing control circuit 30. The various timing and other signals are shown in FIG. 3 and the various letter points on the schematic diagram of FIG. 1 correspond to the signals shown in FIG. 3. The timing control circuit 30 comprises any suitable arrangement of logic circuits for producing the timing signals shown as lines A and F of FIG. 3. This can be, for example, a series of one shot multivibrators which are connected to trigger each other successively or which are free running.

The bursts of clock pulses are produced at a rate generally corresponding to the rate of liquid flow in the tube. That is, the gating pulses which control the passing of the clock pulse bursts to the transmit crystal are produced at a rate so that all segments of the liquid stream are tested with sonic energy as the stream flows past the crystal.

The electrical signals from the clock pulse generator 26 are applied to the transmit crystal 15 where they are converted into ultrasonic energy which is transmitted through the tube 12 and the fluid stream therein to the receive crystal 17. The receive crystal 17 converts the received sonic energy into electrical signals and these are applied to the input of an RF amplifier which has a bandpass sufficiently wide to amplify the received signals.

In general, the sonic energy is transmitted through liquid in the tube with little attenuation. When a discontinuity is encountered, the amplitude of the sonic energy which reaches the receive crystal 17 is reduced. The amount of amplitude reduction depends upon such factors as the size of the discontinuity and, if discontinuities other than air are being checked for, the material of the discontinuity.

The output of RF amplifier 34 is applied to an amplifier stage 36 which gives the system sufficient gain to provide signals to the inputs of two peak detector circuits 40 and 42. In general, as many amplifier stages 34 and 36 can be utilized as is necessary, it being understood that there should be sufficient gain so that sonic signals transmitted through the liquid in the tube provide a readily detectable signal level.

The output of the gain stage amplifier 36 is applied to the input of the first peak detector circuit 40 which has a slow (long) time constant response. In general, the time constant of peak detector 40 is made substantially longer than a large number, for example, several hundred, of the times during which a burst of transmit pulses are produced. Accordingly, detector 40 has no instantaneously changing output in response to individual received signals. However, the long time constant peak detector 40 will establish a reference level signal at its output which is designated as V2. This reference level signal adapts to various system variables which affect the received signal, for example, the type of liquid and its characteristics, temperature, amplifier gain, etc.

The output of the gain stage 36 is also applied to the input of a second peak detector circuit 42 which has a fast (short) time constant response. The time constant of the circuit 42 is made sufficiently short so that the electrical signal corresponding to each burst of transmit pulses will pass through and be detected. The peak detectors 40,42 are of conventional construction and respond to the peak amplitude of the signal (line D of FIG. 3) at the output of gain stage 36.

The slow time constant peak detector circuit 40 also provides an AGC control signal back to the RF amplifier 34. The purpose of this is to normalize the gain of the system such that the output levels of the two peak detectors 40 and 42 are substantially equal at all times in response to system variations, for example, changes in the diameter of the tube 12, either its outside diameter or its wall thickness.

The output V2 of the long time constant peak detector 40 is applied to the input of an attenuator circuit 44 whose output (V3) is applied to one input of a comparator circuit 48. The attenuator can be any suitable voltage divider, potentiometer, adjustable gain feedback amplifier, etc. The other input of the comparator 48 is from the output (V1) of the fast time constant peak detector 42. In general, the comparator 48 will produce an output signal when the signal level at its V1 input from the fast time constant peak detector exceeds the reference level V2 from the slow time constant peak detector after it has been attenuated to a desired level. As described below, this occurs when there is liquid in the tube. When a discontinuity in the tube passes the crystals, the fast time constant peak detector does not have an output signal or has one of a reduced amplitude lower than the reference level V3.

The sensitivity of the circuit is set by the attenuator 44. Raising the reference level V3 means that the V1 signals from the fast time constant peak detector have to have a higher amplitude to causes the comparator 48 to have an output to indicate no discontinuity. Thus, even a small discontinuity, such a a small air bubble, which reduces the signal level (line D of FIG. 3) by only a small amount will cause the V1 signal level to be less than the reference level V3 so that the comparator can discriminate between these also. That is, as the reference level V3 is raised, the system becomes more sensitive and smaller discontinuities are detected.

FIG. 3 is a timing and signal diagram of the circuit for four cycles T1-T2, T2-T3, T3-T4 and T4-. . . . The system timing control system circuit 30 produces a series of periodic gating pulse (line A) during which the clock pulses (line B) are applied to the transmit crystal 15. It also produces a delay signal (line C).

Line D shows the received signal after amplification. In the third cycle, T3-T4, the sonic signal passes through a discontinuity so the received signal is attenuated. The amount of the attenuation depends on the size of the discontinuity relative to the beam of sonic energy (related to crystal) size, produced by the transmit crystal. As more energy is blocked by the discontinuity the amplitude of the signal decreases. The other cycles show the sonic signals after passing fully through the liquid and these are maximum amplitude.

Line E shows the comparison between the various voltages V1 at the output of the fast time constant peak detector and the reference voltages V2 from the slow time constant peak detector and V3 after the latter is attenuated. V3 is shown in dotted lines and its level is adjustable.

The comparator 48 produces an output (FIG. 3, line G) when V1 is higher in amplitude than V3 (FIG. 3, line E). The comparator output is a pulse whose duration generally corresponds to the time V1 exceeds V3. If desired, the comparator output pulse can be used to trigger a suitable pulse shaping circuit, e.g. a Schmidt trigger, but this is not absolutely necessary. When V1 is less than V3, there is no output from the comparator. This is shown in the third cycle T3-T4. Again, setting the reference level voltge V3 determines the sensitivity of the circuit. The higher V3, the greater will be the sensitivity, i.e. smaller discontinuities will be detected.

The output of the comparator 48 is applied to the CLK input of a decision making flip-flop 52, which illustratively is of the D type. The Q output of the flip-flop 52 is applied to the D (data) input of a second D type flip-flop 54 whose Q output is the indicator output for the circuit. The D input of flip-flop 52 is set high by connecting it to the 1 state voltage level.

The timing control circuit 30 includes a one shot multivibrator which produces the timing signal shown on line F of FIG. 3. The timing signal is applied to the reset input of the decision making flip-flop 52 and the CLK input of the indicator flip-flop 54.

The negative going edge of the timing signal of line F resets flip-flop 52. As seen on line F, the timing signal waveform stays low from before and after the time when a signal from the comparator would appear, i.e., it forms a window for a time T. If there is a 1 signal at the output (line G of FIG. 3) of the comparator 48, indicating that there is no discontinuity in the tube 12 and that the sonic signal is passing through liquid, then this clocks flip-flop 52 and sets its state to a logic level 1 at its Q output. This output is connected to the D (data) input on the second flip-flop 54.

After a time delay T which is determined by the RC time constant of the one shot multivibrator in the timing control 30 logic, the timing signal of line F changes state and its positive going edge clocks the second flip-flop 54 and sets the first flip-flop to the off state. The Q output of the second flip-flop 54 goes to a logic level "1" and the $\overline{Q}$ output goes to logic level 0. This is shown at line H of FIG. 3, which is the circuit output, for the first two cycles from T1-T2 and T2-T3.

When a discontinuity passes through the path of the sonic energy in tube 12, the signal to the input of the fast time constant peak detector 42 changes amplitude and the output of the fast time constant detector is such that V1 is less than V3. This results in the production of no change in the comparator output signal. This is shown in the third cycle T3-T4 of FIG. 3, line G.

Consequently, there is no clock input to the decision making flip-flop 52 which has been reset by the negative going edge of the timing signal and its Q output is in the logic 0 state. This results in the data input to the second flip-flop 54 being at logic 0 level. Now, the rising edge of the timing pulse signal (line F) clocks the indicator flip-flop 54 and its Q output goes to logic 0 level, this being indicative of the presence of a discontinuity.

The Q output of the indicator flip-flop 54 drives any type of an indicator (not shown) such as an LED, a relay, provides an input signal to a control circuit, etc. The particular type of indication produced is not a part of the invention.

After the discontinuity passes, the comparator 48 again produces a signal in response to the next sonic signal burst passing through liquid. Thus, the decision making flipflop 52 is clocked and will change its state to produce a 1 on its Q output after first being reset by the negative going edge of the timing control signal F. This applies a logic 1 to the D input of flip-flop 54 and causes the Q output of this flip-flop to go to 1 indicating that there is liquid in the tube.

As should be noted, the indicator flip-flop 54 is configured so that its Q output will always be 0, indicating the presence of a discontinuity, in the absence of the production of a signal by the comparator 48. Thus, any malfunction in the circuit will make the Q output of flip-flop 54 go to 0.

While D type flip-flops have been shown for the decision making and indicator flip-flops, it should be understood that any suitble logic circuits can be used. Also, the 1 and 0 logic and gating levels described can be inverted and the appropriate amplifiers and gates used as is conventional in the art.

What is claimed is:

1. Apparatus for detecting a discontinuity in a stream of fluid flowing in a tube,
   a transmitting transducer and a receiving transducer between which said tube is located,
   means for supplying successive pulses of electrical energy to said tranmitting transducer to cause it to vibrate to produce corresponding pulses of sonic energy signals which are transmitted through said tube to said receiving transducer, said receiving transducer converting the pulses of received sonic signals into corresponding electrical signals,
   means responsive to a plurality of said successive received sonic signals for establishing a signal reference over a relatively long period of time corresponding to the characteristics of fluid flowing in the tube and the characteristics of the tube, and
   means for detecting when a said received sonic energy signal on a substantially instantaneous basis is of a different value than said signal reference level indicating the presence of a discontinuity in the fluid stream.

2. Apparatus as in claim 1 wherein said detecting means operates in response to a signal of lesser amplitude than said signal reference level to indicate the presence of a discontinuity.

3. Apparatus as in claim 2 wherein said means for establishing said signal reference level comprises means for measuring the amplitude of a number of said successive received signals.

4. Apparatus as in claim 1 wherein said means for establishing said signal reference level comprises means for measuring the amplitude of a number of said successive received sonic signals.

5. Apparatus as in claim 4 wherein said means for supplying produces bursts of pulses of electrical energy to causes the production of corresponding bursts of pulses of source energy signals, said means for establishing said signal reference level comprises first detector means having a time constant substantially larger than the time of a burst of sonic energy signals.

6. Apparatus as in claim 5 further comprising attenuator means coupled to the output of said first detector means for setting the amplitude of said signal reference level.

7. Apparatus as in claim 5 further comprising amplifier means between the output of said receiving transducer and the input of said first detector means, and means coupling an automatic gain control signal from the output of said first detector means to said amplifier means.

8. Apparatus as in claim 1 wherein said detecting means comprises a second detector means which produces an output signal corresponding to the amplitude of each successively received sonic energy signal.

9. Apparatus as in claim 5 wherein said detecting means comprises a second detector means which produces an output signal corresponding to the amplitude of each successively received sonic energy signal.

10. Apparatus as in claim 9 wherein said detecting means further comprises comparator means for comparing the amplitudes of the output signals of said first and second detector means.

11. Apparatus as in claim 10 wherein said comparator means produces a first output signal when the amplitude of the output signal from said second detector means exceeds the amplitude of the reference level signal and a second output signal when the amplitude of the output signal from said second detector means is less than the amplitude of said reference level signal.

12. Apparatus as in claim 11 further comprising indicator means coupled to said detecting means and responsive to a said first output signal from said comparator means for indicating the presence of liquid in the tube and to said second output signal from said comparator means for indicating the presence of a discontinuity in said tube.

13. Apparatus as in claim 12 wherein said indicator means is normally set to indicate the presence of a discontinuity in said tube and said first output signal from said comparator means changes its state.

14. Apparatus as in claim 1 wherein said means for supplying produces successive bursts of pulses of electrial energy to cause the production of corresponding bursts of pulses of sonic energy signals.

15. Apparatus as in claim 14 wherein the successive bursts of pulses of sonic energy signals comprise pulses of substantially equal amplitude.

16. Apparatus as in claim 1 wherein said successive transmitted pulses of sonic energy signal are of substantially equal amplitude.

* * * * *